United States Patent [19]

Berman et al.

[11] Patent Number: 5,541,296

[45] Date of Patent: Jul. 30, 1996

[54] MONOCYTE ADHESION PROTEIN AND MONOCLONAL ANTIBODY THERETO

[75] Inventors: Joan W. Berman, New York; Tina M. Calderon, Bronx, both of N.Y.

[73] Assignee: Albert Einstein College of Medicine of Yeshiva University, a Division of Yeshiva University, Bronx, N.Y.

[21] Appl. No.: 357,535

[22] Filed: Dec. 16, 1994

Related U.S. Application Data

[63] Continuation of Ser. No. 869,924, Apr. 16, 1992, abandoned, which is a continuation-in-part of Ser. No. 753,224, Aug. 30, 1991, abandoned.

[51] Int. Cl.$^6$ ..................................................... A61K 35/16
[52] U.S. Cl. ................................. 530/388.22; 530/387.1; 530/389.1
[58] Field of Search ........................... 530/388.22, 387.1, 530/389.1

[56] References Cited

PUBLICATIONS

Martiney Faseb J 5(4) A624 Abst 1469 1991.
Calderon Circulation 82(4):III–94 Abst 0368 1990.
Dixit et al JBC 265(5) 2973–2978 1990.
Lerner Nature 299:592–596 1982.
Harris et al. TibTech 11:42–44 1993.
Wabmann Science 252:1657–1662 1991.
Dialog Dissertation Abstract James A. Martiney.

*Primary Examiner*—Donald E. Adams
*Attorney, Agent, or Firm*—Amster, Rothstein & Ebenstein

[57] ABSTRACT

This invention relates to a method for the prevention of monocyte adherence to the endothelial cells lining blood vessels, their subsequent invasion of surrounding tissues and diseases related thereto. It comprises inducing a monocyte adhesion protein to the surface of endothelial cells by treatment with specific cytokines, preparing a monoclonal antibody to the monocyte adhesion protein and contacting the antibody to the protein to form a complex. The monoclonal antibody does not bind to the cell surface proteins VCAM or ELAM. The complex results in a decrease in the adherence of monocytes to endothelial cells and thereby attenuates or prevents the harmful effects of monocyte invasion of endothelial cells and surrounding tissues.

3 Claims, 8 Drawing Sheets

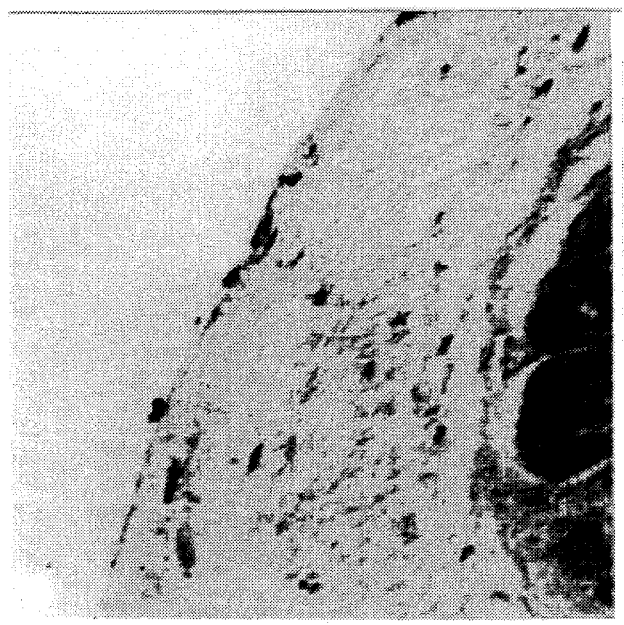
FIG. IIA
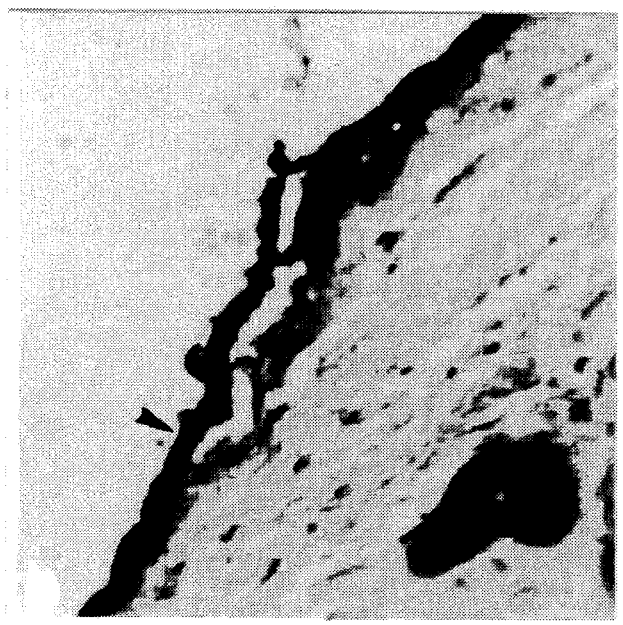
FIG. IIB

MONOCYTE ADHESION PROTEIN AND MONOCLONAL ANTIBODY THERETO

CROSS-REFERENCE TO RELATED APPLICATIONS

This Application is a Continuation of application Ser. No. 07/869,924, filed Apr. 16, 1992, which is abandoned, a Continuation-In-Part of application Ser. No. 07/753,224, filed Aug. 30, 1991, entitled MONOCYTE ADHESION PROTEIN AND MONOCLONAL ANTIBODY THERETO.

FIELD OF THE INVENTION

This invention relates to a method useful in the prevention of monocyte invasion of tissues surrounding blood vessels and diseases related thereto. It comprises the inducement of a monocyte adhesion protein to the surface of human endothelial cells with specific cytokines, the preparation of a monoclonal antibody which binds to this protein and the formation of an antibody-protein complex. The formation of a complex between the cytokine induced monocyte adhesion protein and the monoclonal antibody decreases the adherence of monocytes to the activated endothelial cells, thereby attenuating or preventing the harmful effects of monocyte adhesion to endothelial cells and their subsequent migration into surrounding tissues.

BACKGROUND OF THE INVENTION

Monocytes have been implicated in the pathogenesis of atherosclerosis. The binding of monocytes to endothelial cells which line blood vessel walls is an early event in the development of atherosclerotic lesions. The mechanism by which the monocytes bind to the endothelial cells is unknown. Sites of injury have shown evidence of monocyte adhesion. Therefore, for the prevention and treatment of atherosclerosis and other diseases which involve the invasion of tissues surrounding blood vessels by monocytes, it is necessary to lessen or prevent the adherence of monocytes to endothelial cells. In addition, a decrease in monocyte adherence to endothelial cells may similarly decrease inflammation.

The method of this invention utilizes cytokines to induce a monocyte adhesion protein to the surface of endothelial cells. Cytokines are protein cell regulators, also known as lymphokines, monokines, interleukins and interferons. Cytokines are low molecular weight secreted proteins which are involved in immunity and inflammation, where they regulate amplitude and duration of immunological response. They are usually produced transiently and locally, and interact with high affinity to cell surface receptors specific for each cytokine or cytokine group. Their cell surface binding leads to changes in cellular RNA and protein synthesis culminating in alterations of cell-function. In the present invention, the monocyte adhesion protein induced to the cell surface by the cytokines forms a complex with a monoclonal antibody specific for the protein. As a result, monocyte adherence to endothelial cells is decreased.

U.S. Pat. No. 5,011,778 to Newman, et al. entitled "Monoclonal Antibodies Directed to IL-1 Activated Endothelial Cells and Medicaments Employing the Monoclonal Antibodies", ("the Newman Patent") discloses monoclonal antibodies which bind to proteins on the surface of IL-1 activated endothelial cells, which antibodies do not bind significantly to normal resting endothelial cells and do not bind significantly to normal resting IL-1 activated epidermal keratinocytes or resting IL-1 activated fibroblasts. The monoclonal antibodies disclosed in the Newman Patent are indicated for use in therapeutic compositions for blocking inflammatory responses associated with activated endothelial cells.

The Newman Patent discloses four specific monoclonal antibodies designated IE7, 2G7, 7A9 and 3A2. Monoclonal antibody IE7 blocks the binding of T-cells, B-cells, NK cells and monocytes to proteins on the surface of IL-1 activated endothelial cells. Monoclonal antibody IE7 binds to the protein VCAM. Further, proteins to which monoclonal antibody IE7 bind have, under non-reducing conditions on SDS-PAGE, a major band at 99 kD and a minor band at 97 kD. Further, the IE7 monoclonal antibody binds to proteins on the surface of IL-1-treated endothelial cells which proteins have chronic expression (i.e., have maximal expression on the surface of the endothelial cells for 72–96 hours).

Monoclonal antibody 2G7 of the Newman Patent blocks the binding of T-cells, B-cells and monocytes to proteins on the surface of IL-1-treated endothelial cells. Monoclonal antibody 2G7 also binds to the protein VCAM. Further, monoclonal antibody 2G7 reacts with proteins which, under non-reducing conditions on SDS-PAGE, have a major band at 99 kD and a minor band at 87 kD. In addition, monoclonal antibody 2G7 binds to proteins on the surface of IL-1-treated endothelial cells, which proteins have chronic expression (i.e., have maximal expression for 72–96 hours).

Monoclonal antibody 7A9 of the Newman Patent blocks the binding of granulocytes and monocytes to proteins on the surface of IL-1-treated endothelial cells. Monoclonal antibody 7A9 binds to the protein ELAM. Further, the 7A9 monoclonal antibody binds to proteins which, under non-reducing conditions on SDS-PAGE, show a band at 90 kD. In addition, the 7A9 monoclonal antibody binds to proteins on the surface of IL-1-treated endothelial cells which proteins have chronic expression (i.e., have maximal expression for 72–96 hours).

Monoclonal antibody 3A2 of the Newman Patent binds to proteins which, under non-reducing conditions on SDS-PAGE, show a major band at 177 kD and a minor band at 57 kD. Further, the 3A2 monoclonal antibody binds to proteins which have acute expression on the surface of IL-1-treated endothelial cells (i.e., the expression of such proteins decreases and disappears by 24 hours).

The monoclonal antibodies of the Newman Patent bind to the proteins VCAM and ELAM, which proteins are induced to the surface of endothelial cells with cytokines. The monoclonal antibody of the present invention does not bind to either VCAM or ELAM. Instead, the monoclonal antibody binds to a different monocyte adhesion protein.

To date, no protein has been discovered, purified or induced to the surface of endothelial cells wherein the forming of a complex between such protein and a monoclonal antibody for such protein prevents the adherence of monocytes to such endothelial cells without preventing the adherence of T-cells, B-cells, NK cells, granulocytes, lymphocytes or other white blood cells to such endothelial cells, thereby more effectively reducing monocyte invasion of blood vessels and diseases related thereto. The present inventors have induced a protein to the surface of endothelial cells and have raised monoclonal antibody to such protein. The formation of a complex between such protein and monoclonal antibody on the surface of endothelial cells results in the prevention of monocyte adherence to such endothelial cells, but not the adherence of other white blood cells. It is believed that this specificity for monocytes is advantageous in the treatment and prevention of monocyte induced or oriented inflammation and diseases.

It is an object of this invention to provide a method for reducing monocyte adherence to endothelial cells lining blood vessels.

It is another object of this invention to provide a method for reducing monocyte invasion of blood vessels surrounding tissues.

It is a further object of this invention to provide a method for reducing diseases related to monocyte adherence to endothelial cells lining blood vessels and invasion of blood vessels surrounding tissues.

It is still a further object of this invention to induce a monocyte adhesion protein to the surface of endothelial cells and to produce a monoclonal antibody thereto wherein the formation of a complex between such protein and monoclonal antibody specifically blocks the adherence of monocytes to said endothelial cells but does not block the adherence of other white blood cells to said endothelial cells.

It is another object of this invention to produce a monoclonal antibody specific for proteins recognized by monocytes but not recognized by other white blood cells.

SUMMARY OF THE INVENTION

This invention relates to the inducement of a monocyte adhesion protein to the surface of human endothelial cells by activation of the endothelial cells with specific cytokines, the preparation of a monoclonal antibody which binds to this protein and the formation of an antibody-protein complex. When the cytokine-induced monocyte adhesion protein on the surface of the endothelial cells and the monoclonal antibody thereto react to form a complex, the adherence of monocytes to the endothelial cells is decreased. The monocyte adhesion protein recognized by the monoclonal antibody is not cell surface proteins VCAM or ELAM. This complex does not prevent the adherence of T-cells, B-cells, NK cells, granulocytes or other white blood cells to activated endothelial cells. This decrease in adherence of monocytes to endothelial cells may result in the reduction of harmful effects caused by monocyte invasion of tissues surrounding blood vessels.

BRIEF DESCRIPTION OF THE DRAWINGS

The above brief description, as well as further objects and features of the present invention, will be more fully understood by reference to the following detailed description of the presently preferred, albeit illustrative, embodiment of the present invention when taken in conjunction with the accompanying drawings wherein:

FIGS. 11a and 11b represents the reactivity of monoclonal antibody IG9 with endothelial cells lining an arterial vessel in a healing human myocardial infarction.

DETAILED DESCRIPTION OF THE INVENTION

Figure 1:
FIG. 1 represents expression of the IG9 monocyte adhesion protein on the surface of TNFα treated endothelial cells.

Monocyte adherence to the endothelial cell lining of blood vessels has been implicated in the pathogenesis of atherosclerosis and other diseases, including disseminated intravascular coagulation (DIC). Therefore, if monocyte invasion of tissues surrounding blood vessels can be reduced or eliminated, atherosclerosis, DIC and other diseases similarly provoked may be attenuated in their initial stages, and possibly reduced altogether. In order to invade the tissue surrounding blood vessels, monocytes bind with endothelial cells which line blood vessel walls. The purpose of this invention is to reduce or prevent the binding of monocytes to endothelial cells, and to treat and prevent diseases caused by monocyte adherence to endothelial cells and their migration into surrounding tissue. In addition, this invention may serve to reduce inflammation.

The invention comprises inducing a monocyte adhesion protein to the surface of human endothelial cells with specific cytokines. Cytokines which may be used for this purpose are TNFα, IL-1α and IL-1β. However, it is possible that other cytokines may also be used for this purpose.

This invention further comprises producing a monoclonal antibody to the monocyte adhesion protein and forming an antibody-protein complex. When the monoclonal antibody and the monocyte adhesion protein on the surface of the endothelial cells form a complex, the ability of monocytes to adhere to the endothelial cells upon which the complex exists is decreased. This decrease in the adherence of monocytes to activated endothelial cells may result in a reduction of hemorrhage, inflammation, and attenuation of the initial stages of atherosclerosis, DIC and other diseases provoked by monocyte adherence to endothelial cells and their subsequent migration into surrounding tissues. However, while the formation of this complex prevents monocytes from adhering to activated endothelial cells, it does not prevent the adherence of T-cells, B-cells, NK cells, granulocytes, lymphocytes or other white blood cells to such activated endothelials.

EXAMPLE #1

Preparation of Endothelial Cells

Human umbilical Vein Endothelial cells (HUVE) were harvested from human umbilical veins and maintained in tissue culture. The cells were grown to confluency in gelatin-coated 100 mm tissue culture dishes (Falcon Labware, Oxnard, Calif.) and maintained at 37° C. and 5% $CO_2$. The cell culture medium contained Medium 199 (M199, Grand Island Biological Company, Grand Island, N.Y.) and was supplemented with 15 mM HEPES (Calbiochem-Behring, La Jolla, Calif.), 25 μg/ml of heparin (Sigma Chemical Company, St. Louis, Mo.), 10% human and 20% newborn calf serum (Gibco), 1.5 mM glutamine (Sigma Chemical Company) and 3 mg % partially purified acidic fibroblast growth factor extracted from bovine brain. Cell type was confirmed by the typical cobblestone morphology observed in tissue culture and by the presence of Von Willebrand factor antigen.

Treatment with Cytokines

The medium was removed from the cells and replaced with fresh medium containing TNFα (100 units/ml). The cells were then incubated at 37° C., 5% $CO_2$ for 5 hours to induce the monocyte adhesion protein to the surface of the endothelial cells. After treating The cells with TNFα, the cells were collected by gentle scraping, pelleted, and half of the cells were fixed with 0.1% glutaraldehyde.

Other cytokines which may be used to induce the monocyte adhesion protein to the surface of endothelial cells are IL-1α and IL-1β, with endotoxin levels of <1.5 endotoxin units per ml ($6.6 \times 10^7$ U/mg protein).

Preparation of Monoclonal Antibodies

Mice (BALB/c F) were injected intraperitoneally with a 1:1 mixture of fixed and unfixed cells (107 total) in saline. The procedure was repeated twice, every other week. One week after the last boost, the sera of the animals was tested for reactivity to TNFα treated endothelial cells by ELISA.

After the ELISA was performed, the animal with the highest titered serum was again boosted intraperitoneally, and 2 days later its spleen was removed for fusion with NSO myeloma cells. The fusion of the antibody-producing B-lymphocytes from the spleen with the NSO myeloma cells resulted in a hybridoma which produces a monoclonal antibody, designated monoclonal antibody IG9, which monoclonal antibody is reactive with the monocyte adhesion protein (IG9 monocyte adhesion protein) which was induced to the surface of the endothelial cells with TNFα. The, hybridoma which secretes the IG9 monoclonal antibody was deposited with the American Type Culture Collection, Rockville, Md. on Apr. 16, 1992, and catalogued as ATCC # HB11023.

In order to perform the ELISA, the endothelial cells were plated onto 96 well collagen-coated microtiter dishes, and at confluence, the cells were treated with 100 μl TNFα for 5 hours. The cultures were then washed and fixed in 0.1% glutaraldehyde. Hybridoma culture supernate (100 Ul) was added to each well for 90 minutes at 37° C. After several washes, a mixture of alkaline phosphatase-coupled goat anti-mouse immunoglobulins (GAMIG) was added for 90 minutes at 37° C. The cells were washed four times, and substrate (P-Nitrophenyl phosphate, disodium) was added. After 10–30 minutes, the reactivity was determined spectrophotometrically. To detect only surface reactivity, the endothelial cells were fixed with 1% formaldehyde.

The endothelial cells were then plated onto collagen-coated LAB-TEK four chamber slides. After 24 hours, they were treated with TNFα (100 units/ml) for varying amounts of time, and were washed and fixed with 1% formaldehyde. The cells were then treated with 200 μl of culture supernate or purified antibody (1:500), with fluoresceinated GAMIG and were examined microscopically.

Results

The IG9 monocyte adhesion protein, under non-reducing conditions on SDS-PAGE, has a major band at 105 kD and a minor band at 57 kD. The IG9 protein appears on the surface of activated endothelial cells after 3 hours, is maximally expressed for 4–9 hours, declines at 24 hours and is undetectable at 48 hours. This protein is neither VCAM nor ELAM, which proteins have been previously identified on the surface of cytokine-activated endothelial cells. This protein is recognized on activated endothelial cells which line blood vessels where there is inflammation and/or atherosclerotic plaque (see FIGS. 7 and 8), on coronary artery endothelium overlying atherosclerotic plaque where there are lesions (see FIG. 9), in WHHL rabbit aorta where there is atherosclerotic plaque (see FIG. 10), and in arterial vessels in healing myocardial infarction (see FIGS 11a and 11b).

The prepared IG9 monoclonal antibody to the IG9 monocyte adhesion protein, which is an $IgG_3$ isotype antibody, blocks the adhesion of the human promyelomonocytic cell line, U937, to TNF treated endothelial cells by 35–40%, and has no effect on U937 cell binding to untreated endothelial cells. This monoclonal antibody does not block T-cell, B-cell, NK cell, lymphocyte or granulocyte adhesion to TNF treated endothelial cells. Further, the IG9 monoclonal antibody does not bind to resting endothelial cells, resting monocytes, tissue fibroblasts, smooth muscle cells, mononuclear cells, or alveolar macrophages. The IG9 monoclonal antibody does bind to TNF activated endothelial cells, IL-1 activated endothelial cells and olipopolysaccharide activated endothelial cells. This antibody, while binding to the IG9 monocyte adhesion protein of this invention, does not bind to either VCAM or ELAM proteins, which proteins may also be induced to the surface of endothelial cells with cytokines. Both the IG9 monocyte adhesion protein and the IG9 monoclonal antibody appear to be involved specifically in monocyte-endothelial cell interactions.

FIG. 1 shows endothelial cell surface localization of the IG9 monocyte adhesion protein as detected by electron microscopy. HUVE plated on gelatin-coated 4 chamber Lab-Tek slides were treated with medium-containing TNFα (100 U/ml) for 24 hours, fixed with 2% paraformaldehyde, 0.25% glutaraldehyde and incubated with IG9 monoclonal antibody supernatant followed by biotinylated goat anti-MIG and streptavidin particles. The small dark particles on the cell surface of a TNFα treated HUVE cells can be seen in this electron micrograph and illustrate the even distribution of the IG9 monocyte adhesion protein on the activated endothelial cell membranes.

Figure 2:
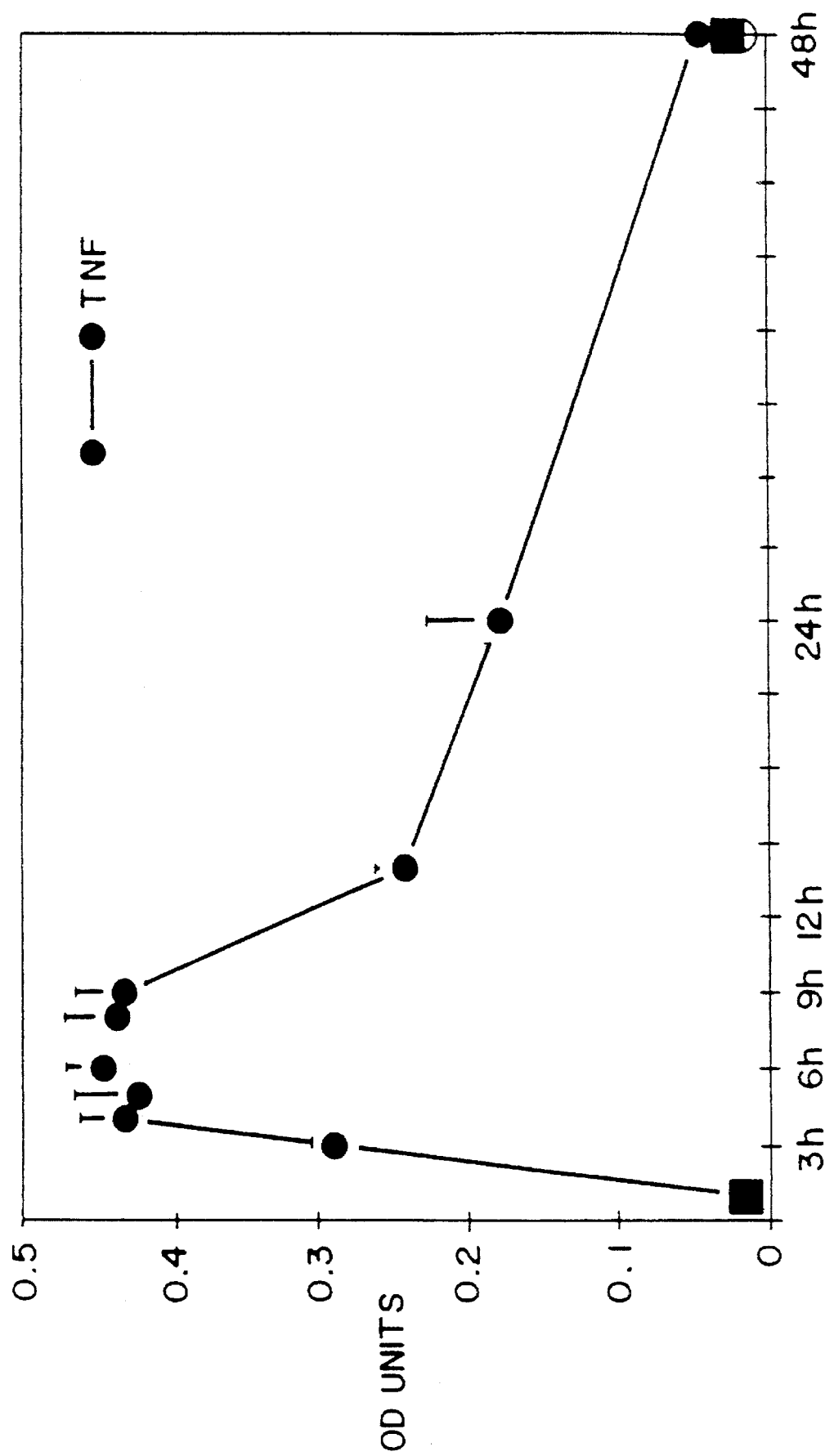
FIG. 2 represents expression of the IG9 monocyte adhesion protein on the surface of TNFα treated endothelial cells as detected by ELISA utilizing monoclonal antibody IG9, and shows the amount of time required for the expression of the IG9 monocyte adhesion protein on the surface of the activated endothelial cells.

FIG. 2 shows the expression of the IG9 monocyte adhesion protein on the surface of TNFα treated endothelial cells as detected by ELISA. HUVE plated on gelatin-coated 96-well plates were treated with medium containing TNFα (100 U/ml) for varying periods of time. Cell surface expression was detected using the IG9 monoclonal antibody supernatant after fixation of the HUVE with 1% formaldehyde in PBS. FIG. 2 also shows the amount of time required for expression of the IG9 monocyte adhesion protein on the surface of the activated endothelial cells, which was 3 hours.

Figure 3:
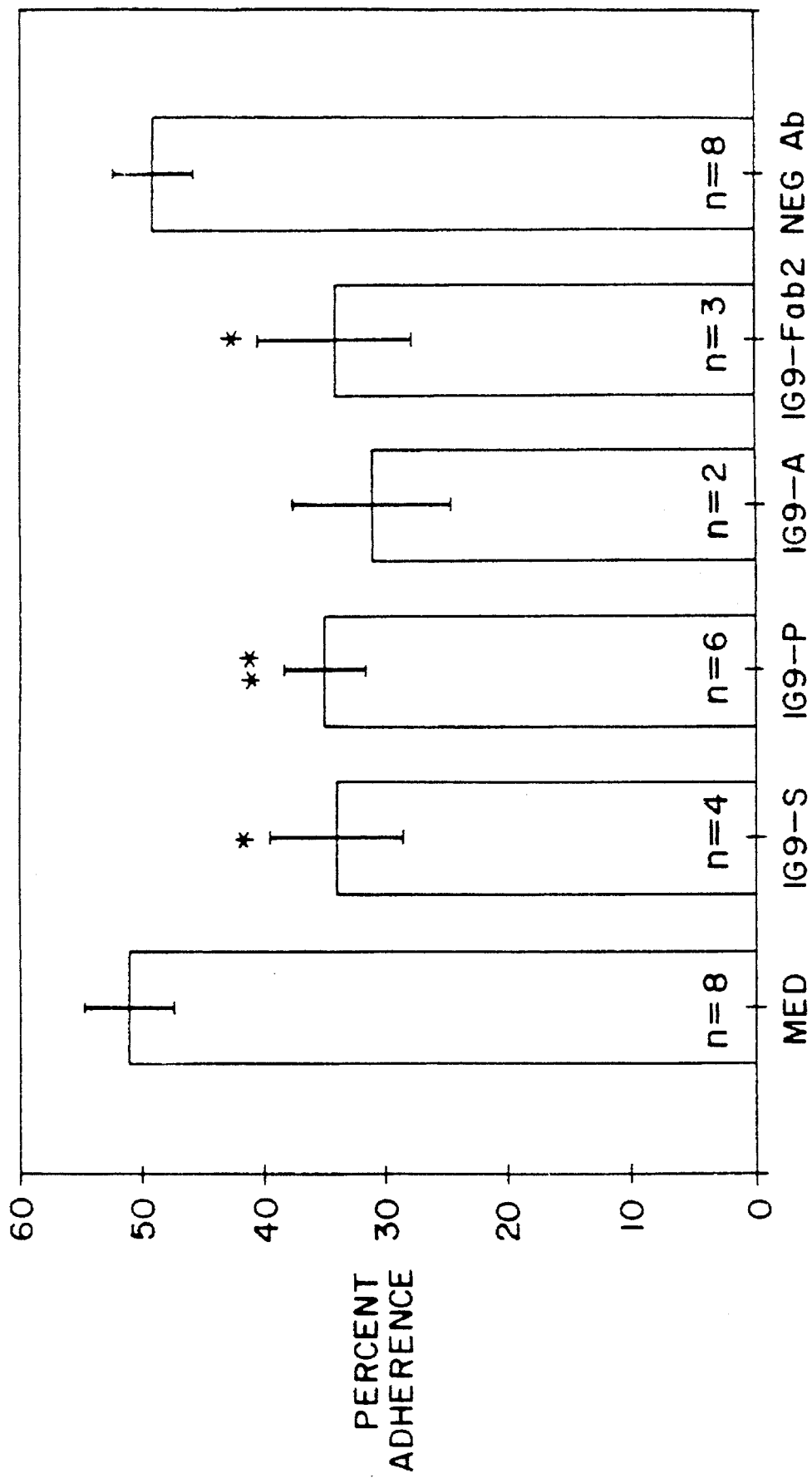
FIG. 3 represents the binding of various preparations off monoclonal antibody IG9 to TNFα treated endothelial cells, and thereby shows that the IG9 monoclonal antibody inhibits U937 monocyte cell adherence to the TNFα treated endothelial cells.

FIG. 3 shows the binding of various preparations of the IG9 monoclonal antibody to TNFα treated endothelial cells. MED is the medium used wherein HUVE were treated with medium alone before the adhesion of the U937 monocyte cells. Since there was no antibody present in the medium, the percent adherence was the control value, and the inhibitory effect of the different antibody preparations on U937 cell adherence was compared to this control value. IG9-S is the hybridoma supernatant from cells making the IG9 monoclonal antibody. This preparation contained approximately 0.05 mg/ml antibody. IG9-P indicates that the IG9 monoclonal antibody was purified from hybridoma supernatant by passage through Bakerbond ABx Prepscale (J. T. Baker, Phillipsburg, N.J.) columns. This preparation contained approximately 0.4 mg/ml antibody. IG9-A is the ascites fluid from mice injected with the IG9 hybridoma cells. This preparation contained approximately 0.9–9 mg/ml antibody. IG9-F(ab')$_2$ is where ascites were used to isolate F(ab')$_2$ fragments after pepsin digestion. This preparation contained approximately 0.36 mg/ml antibody and did not contain the Fc portion of the IG9 monoclonal antibody, which may contribute to the non-specific interaction of antibodies with endothelial cells. Neg Ab is two different monoclonal antibodies that did not react with HUVE. These were used as negative control antibodies. These were included in the U937 cell adhesion assay to show that the inhibition of adhesion by the IG9 monoclonal antibody was not a non-specific event mediated by any antibody. FIG. 3 shows that the IG9 monoclonal antibody inhibits U937 monocyte cell adherence to the TNFα treated endothelial cells.

Figure 4:
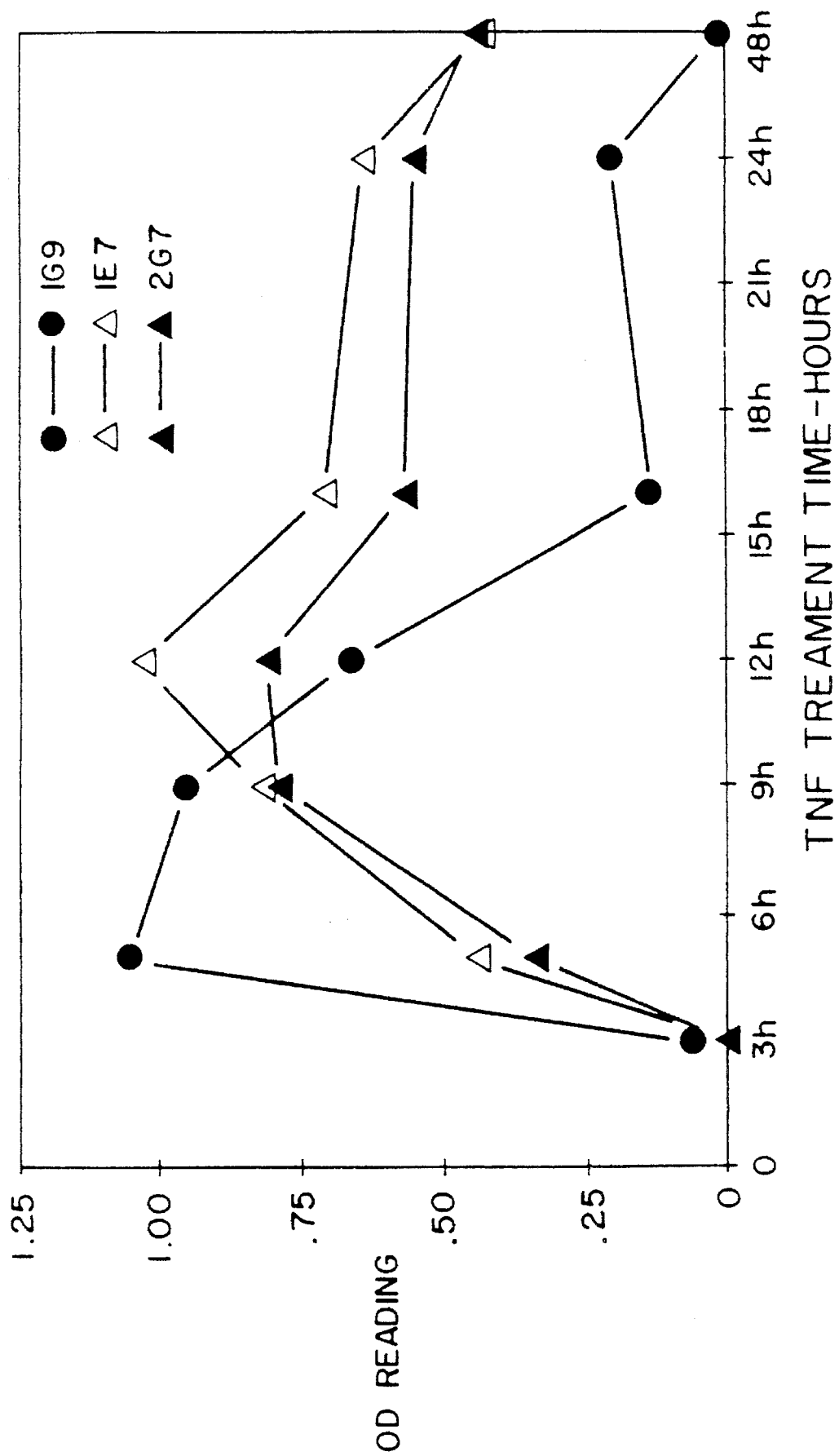
FIG. 4 represents the binding of monoclonal antibody IG9 to the IG9 monocyte adhesion protein, compared with the binding of the Newman Patent monoclonal antibodies IE7 and 2G7 to the protein VCAM as shown by ELISA.

FIG. 4 represents the binding of monoclonal antibody IG9 to the IG9 monocyte adhesion protein. It also compares the binding of the Newman Patent antibodies IE7 and 2G7 to the protein VCAM. VCAM was expressed at a much later time than the IG9 protein. This shows that the IG9 protein is not VCAM, and that the IG9 monoclonal antibody, which binds to the IG9 protein and not to VCAM, is different than the IE7 and 2G7 monoclonal antibodies. This is shown by ELISA.

Figure 5:
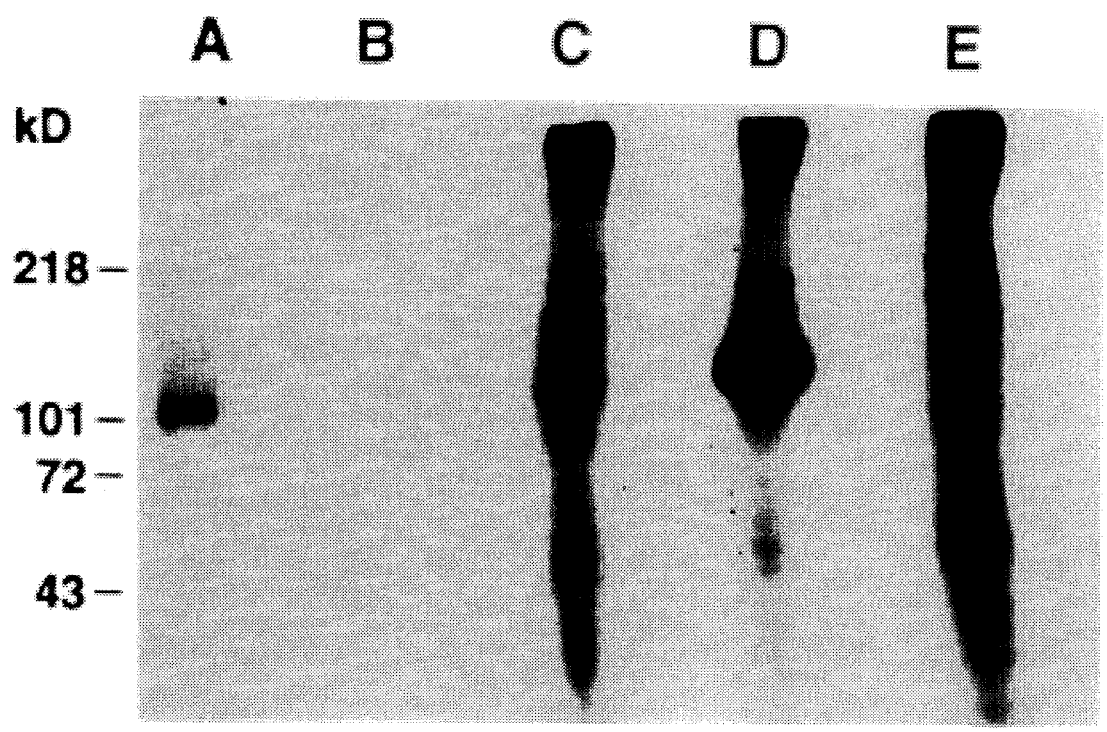
FIG. 5 represents the binding of monoclonal antibody IG9 to the IG9 monocyte adhesion protein, compared with the binding of the Newman Patent monoclonal antibody 2G7 to the protein VCAM as shown by immunoprecipitation.

FIG. 5 shows the binding of monoclonal antibody IG9 to the IG9 monocyte adhesion protein. The binding is also compared with the binding of the Newman Patent monoclonal antibody 2G7 to the protein VCAM. This is shown by immunoprecipitation. The proteins on the surface of the HUVE cells treated with TNFα for 8.5 hours were labeled with $^{125}$I followed by detergent solubilization of the cells. This protein lysate was divided into five equal aliquots. Lane C shows the immunoprecipitation of one aliquot with the IG9 antibody, while lane D shows an immunoprecipitation with the 2G7 antibody. Lane E shows an immunoprecipitation with a negative control antibody. In lanes A and B, two aliquots of protein lysate were pre-cleared twice with antibody 2G7. One aliquot was then immunoprecipitated with the IG9 antibody (lane A), and the other was imunoprecipitated with the 2G7 antibody (lane B). Pre-clearing with the 2G7 antibody removed all of the protein recognized by this antibody so that a subsequent immunoprecipitation with the 2G7 antibody did not produce any protein (lane B). However, pre-clearing with the 2G7 antibody did not significantly effect the amount of the 105 kD IG9 protein immunoprecipitated by the IG9 antibody (lane A). These results show that the protein recognized by the IG9 antibody is different from the protein recognized by the 2G7 antibody.

Figure 6:
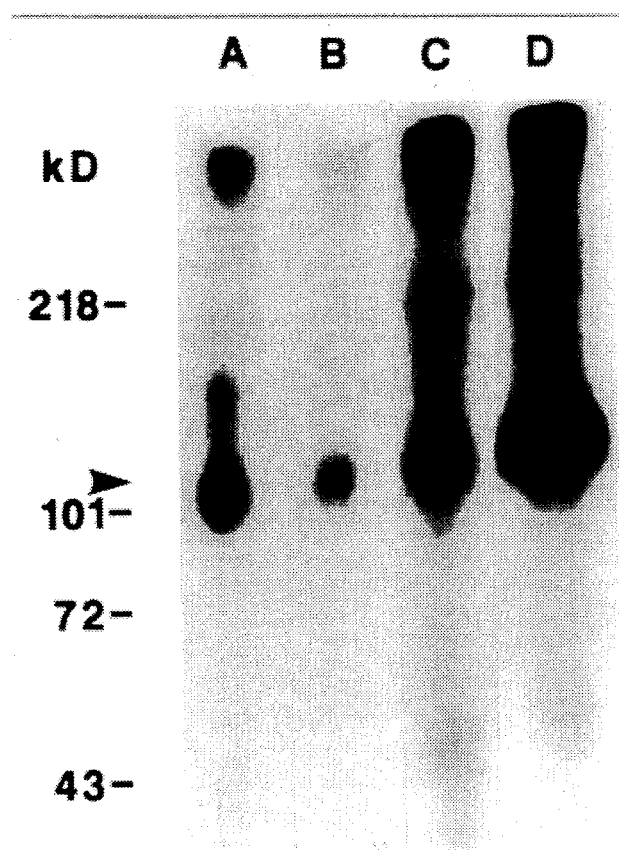
FIG. 6 represents the binding of monoclonal antibody IG9 to the IG9 monocyte adhesion protein, compared with the binding of monoclonal antibody 3B7, which recognizes the same protein as the Newman Patent monoclonal antibody 7A9, to the protein ELAM as shown by immunoprecipitation.

FIG. 6 shows the binding of monoclonal antibody IG9 to the IG9 monocyte adhesion protein of the invention. It compares such binding with the binding of monoclonal antibody 3B7 to the protein ELAM as shown by immunoprecipitation. Monoclonal antibody 3B7 recognizes the same protein as the Newman Patent monoclonal antibody 7A9. To perform this immunoprecipitation, HUVE cells were treated with a medium containing TNFα (100 U/ml) for 5 hours, and cell surface proteins were iodinated with $^{125}$I-Na followed by detergent solubilization. The labeled HUVE protein lysate was divided into four aliquots. Two of the aliquots were pre-cleared twice with monoclonal antibody 3B7, which is an anti-ELAM antibody (see lanes A and B). The remaining two aliquots were uncleared (see lanes C and D). Immunoprecipitation of uncleared aliquots of protein lysate with the IG9 monoclonal supernatent (lane C) or monoclonal antibody 3B7 (lane D) are shown. The immunoprecipitation of a significantly diminished amount of ELAM by monoclonal antibody 3B7 following pre-clearance of the protein lysate with monoclonal antibody 3B7 is shown in lane B. The minimal effects of pre-clearance of monoclonal antibody 3B7 on the immunoprecipitation of the IG9 adhesion protein is also shown.

Chimeric antibodies which contain mouse variable region sequences joined to human constant regions may be genetically engineered using the murine IG9 monoclonal antibody of this invention. Once the IG9 mouse monoclonal antibody is sequenced, the DNA encoding the mouse variable region, which comprises the antigen binding site, can be ligated to DNA encoding human constant regions and this construct can be inserted into an immunoglobulin expression vector. Transfection of murine non-producing hybridoma cell lines with this hybrid construct will produce a hybridoma cell line that will secrete a mouse/human monoclonal antibody that has retained the antigen specificity of the mouse IG9 monoclonal antibody. This chimeric antibody may be injected into humans to attenuate or prevent the harmful effects of monocyte adhesion to endothelial cells and their subsequent migration into surrounding tissues.

EXAMPLE #2

To test the ability of the prepared IG9 monoclonal antibody to modulate inflammation in vivo, IL-1-induced inflammation in the rabbit retina was used as a model. The IG9 monoclonal antibody isolated by the procedure outlined in EXAMPLE #1 was injected intraperitoneally into a rabbit at the same time as the intraocular injection of IL-1 and a few times during the following 6 or 24 hours.

The results of the injections of the IG9 antibody showed a marked decrease in the inflammatory responses normally seen when IL-1 is injected in the rabbit retina. The number of monocytes in and around the retinal blood vessels were reduced and vascular permeability was greatly decreased. Thus, the IG9 antibody recognized the protein induced on the surface of the endothelial cells lining the retinal blood vessels of the rabbit after they were exposed to IL-1. When the IG9 antibody forms a complex with this protein, monocyte binding to the endothelial cells lining the retinal blood vessels is reduced and therefore migration into the surrounding tissue area is also reduced. This results in a decrease in the normal inflammatory responses elicited by the injection of IL-1 as well as a decrease in IL-1 induced vascular permeability.

EXAMPLE #3

Figure 7:
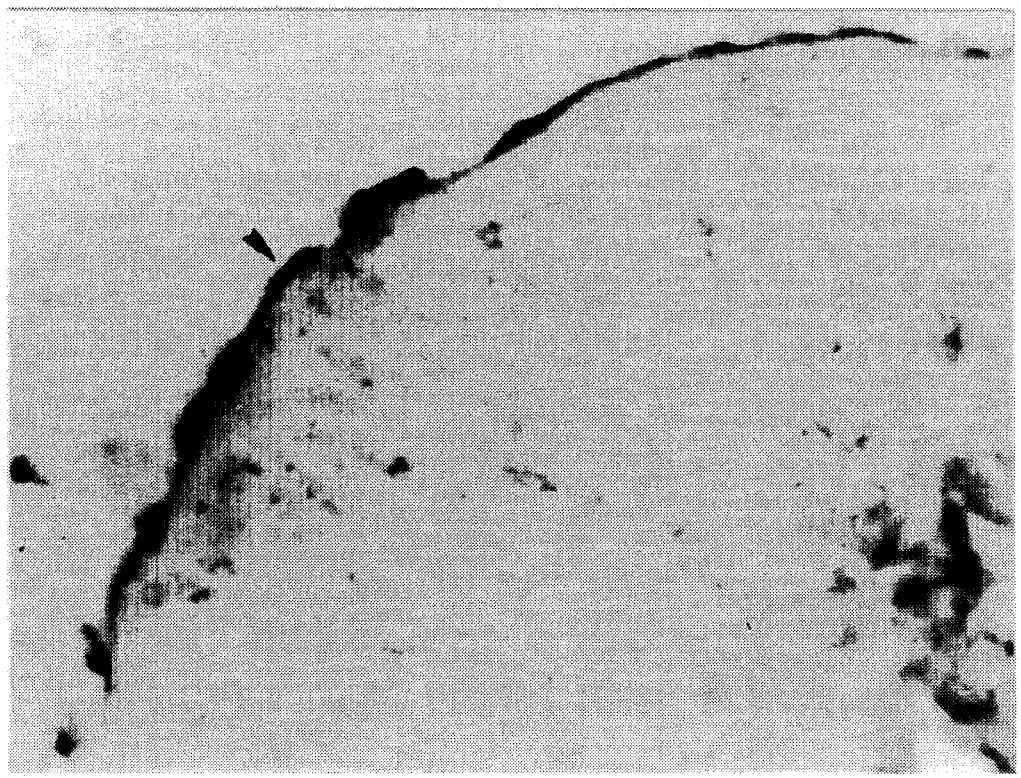
FIG. 7 represents the reactivity of monoclonal antibody IG9 with endothelial cells lining a blood vessel in a tissue section of human lung with extensive inflammation.

The effect of the prepared monoclonal antibody on the development of atherosclerosis in vitro was further tested. The monoclonal antibody isolated by the procedure outlined in Example #1 was tested for reactivity with endothelial cells lining vessels with evidence of atherosclerotic lesions. FIG. 7 shows the reactivity of the IG9 monoclonal antibody with endothelial cells lining a blood vessel in a tissue section of human lung with extensive inflammation. A paraffin-embedded tissue section was analyzed by immunoalkaline phosphatase staining. The endothelial cells lining the vessel exhibited strong reactivity with the IG9 monoclonal antibody.

Figure 8:
FIG. 8 represents the reactivity of monoclonal antibody IG9 with endothelial cells overlying a human atherosclerotic plaque.

FIG. 8 represents the reactivity of the IG9 monoclonal antibody with endothelial cells overlying a human atherosclerotic plaque. A complex atherosclerotic plaque from a human coronary artery exhibited monoclonal antibody IG9 ascites reactivity with the endothelial cells (see arrow).

Figure 9:
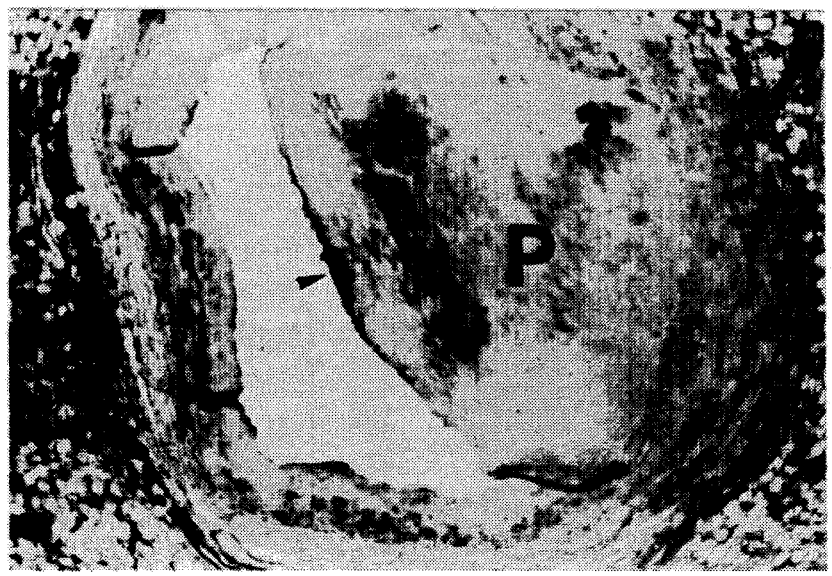
FIG. 9 represents the reactivity of monoclonal antibody IG9 with the endothelial cells overlying an atherosclerotic plaque where there is lesion involvement.

FIG. 9 represents the reactivity of monoclonal antibody IG9 with the endothelial cells overlying an atherosclerotic plaque where there is lesion involvement. A critically narrowed human coronary artery with asymmetrical, complex atherosclerotic plaque (P) exhibited specific endothelial cell reactivity in areas of lesion involvement. Sections of coronary arteries representing a range of lesion involvement from 17 different individuals were analyzed. Vessels with any evidence of pathology in each of the cases examined were reactive with the IG9 monoclonal antibody, while uninvolved vessels were unreactive.

Figure 10:
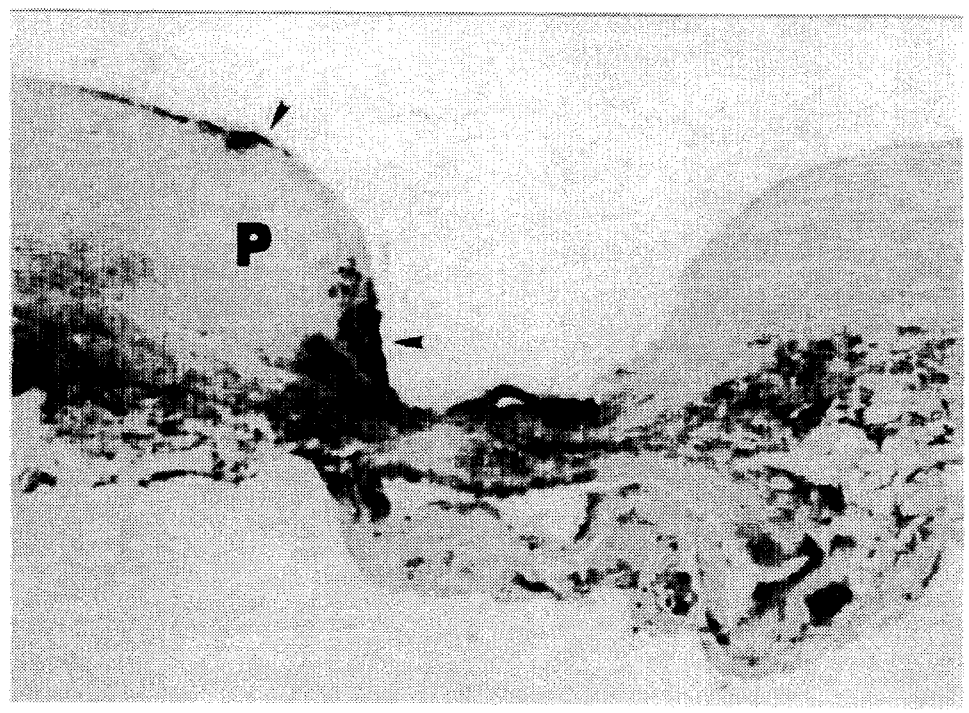
FIG. 10 represents the reactivity of monoclonal antibody IG9 with endothelial cells overlying an atherosclerotic plaque in the aorta of a WHHL rabbit.

Preliminary in vitro experiments using the hypercholesterolemic Watanabe rabbit have shown that the monoclonal antibody reacts with endothelial cells in rabbit vessels with atherosclerotic lesions. FIG. 10 represents the reactivity of monoclonal antibody IG9 with endothelial cells overlying an atherosclerotic plaque in the aorta of a WHHL rabbit. The endothelial cells overlying an atherosclerotic plaque (P) present at the shoulder of a branch point reacted with monoclonal antibody IG9 (see arrows). The rabbit may therefore provide an animal model in which the role of the monocyte adhesion protein on endothelial cells in the development of atherosclerosis in vivo may be studied and determined.

Immunohistochemical studies of sections from human heart transplants and myocardial infarcts with inflammatory cells have shown that this protein is expressed on endothelial cells lining vessels around which monocytes are detected. Uninvolved vessels have shown no reactivity. FIGS. 11a and 11b represent the reactivity of monoclonal antibody IG9 with endothelial cells lining an arterial vessel in a healing human myocardial infarction. There was intense endothelial reactivity with monoclonal antibody IG9 (see arrow).

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A monoclonal antibody which binds to the same monocyte adhesion protein located on the surface of endothelial cells as monoclonal antibody secreted by hybridoma 11023 deposited with the American Type Culture Collection, which protein is not VCAM or ELAM.

2. Hybridoma cell line ATCC No. HB11023.

3. Monoclonal antibody produced by the hybridoma cell line of claim 2.

* * * * *